United States Patent
McAllister et al.

(10) Patent No.: US 7,303,726 B2
(45) Date of Patent: Dec. 4, 2007

(54) MINIMAL PROCEDURE ANALYTE TEST SYSTEM

(75) Inventors: Devin McAllister, San Jose, CA (US); Lorin Olson, Scotts Valley, CA (US); Borzu Sohrab, Los Altos, CA (US)

(73) Assignee: Lifescan, Inc., Milpitas, CA (US)

( * ) Notice: Subject to any disclaimer, the term of this patent is extended or adjusted under 35 U.S.C. 154(b) by 312 days.

(21) Appl. No.: 10/142,443

(22) Filed: May 9, 2002

(65) Prior Publication Data

US 2003/0212345 A1 Nov. 13, 2003

(51) Int. Cl.
*G01N 33/49* (2006.01)

(52) U.S. Cl. ............... 422/68.1; 436/164; 436/166; 436/169; 422/61

(58) Field of Classification Search .......... 436/63, 436/66, 164, 166, 169; 422/58, 61, 68.1
See application file for complete search history.

(56) References Cited

U.S. PATENT DOCUMENTS

| | | |
|---|---|---|
| 5,035,704 A | 7/1991 | Lambert et al. |
| 5,306,623 A | 4/1994 | Kiser et al. |
| 5,510,266 A | 4/1996 | Bonner et al. |
| 5,575,403 A | 11/1996 | Charlton et al. |
| D381,591 S | 7/1997 | Rice et al. |
| 5,708,247 A | 1/1998 | McAleer et al. |
| 5,719,034 A | 2/1998 | Kiser et al. |
| 5,736,103 A | 4/1998 | Pugh |
| 5,757,666 A | 5/1998 | Schreiber et al. |
| 5,797,639 A | 8/1998 | Jaeger |
| 5,820,570 A | 10/1998 | Erickson et al. |

(Continued)

FOREIGN PATENT DOCUMENTS

EP 0 826 963 3/1998

(Continued)

OTHER PUBLICATIONS

The New England Journal of Medicine, vol. 329:977-986, The Effect of Intensive Treatment of Diabetes on the Development and Progression of Long-Term Complications in Insulin-Dependent Diabetes Mellitus, Sep. 30, 1993.

*Primary Examiner*—Lyle A. Alexander
(74) *Attorney, Agent, or Firm*—Wayne C. Jaeschke, Jr.

(57) ABSTRACT

A system employing an integrated analyte test strip including a biosensor and lancet is disclosed. The integration of lancet and the sensor elements eliminates the need to align the sensor to the biologic fluid sample after a lancet and lancing device are used in combination to pierce the skin. The system preferably includes a device comprising two body portions that slide relative to each other to both cock and fire a test strip at a target site. Meter reading and test strip disposal may be accomplished by removing the device from the target site. The device preferably employs a magazine loaded with test strips, with one strip being taken from the magazine each time the device is actuated. It preferably also includes a magazine in a cap to store spent test strips for disposal. The device may be turned on an off simply by removal and return of the cap.

27 Claims, 8 Drawing Sheets

U.S. PATENT DOCUMENTS

| | | | |
|---|---|---|---|
| 5,971,941 A * | 10/1999 | Simons et al. | 600/573 |
| 6,027,459 A | 2/2000 | Shain et al. | |
| 6,056,701 A | 5/2000 | Duchon et al. | |
| 6,063,039 A | 5/2000 | Cunningham et al. | |
| 6,071,251 A | 6/2000 | Cunningham et al. | |
| 6,099,484 A | 8/2000 | Douglas et al. | |
| 6,162,397 A | 12/2000 | Jurik et al. | |
| 6,183,489 B1 | 2/2001 | Douglas et al. | |
| 6,228,100 B1 | 5/2001 | Schraga | |
| 6,241,862 B1 | 6/2001 | McAleer et al. | |
| 6,283,926 B1 | 9/2001 | Cunningham et al. | |
| 6,332,871 B1 | 12/2001 | Douglas et al. | |
| 6,352,514 B1 | 3/2002 | Douglas et al. | |
| 2002/0052618 A1 | 5/2002 | Haar et al. | |

FOREIGN PATENT DOCUMENTS

| | | |
|---|---|---|
| WO | WO 99/44508 | 9/1999 |
| WO | WO 99/64580 | 12/1999 |
| WO | WO 00/74763 | 12/2000 |
| WO | WO 01 00090 | 1/2001 |
| WO | WO 01/23885 | 4/2001 |
| WO | WO 01/63272 | 8/2001 |
| WO | WO 01/64105 | 9/2001 |
| WO | WO 01/67099 | 9/2001 |
| WO | WO 02 08753 | 1/2002 |

* cited by examiner

MINIMAL PROCEDURE ANALYTE TEST SYSTEM

FIELD OF THE INVENTION

This invention relates to systems for obtaining physiologic fluid samples. More particularly, a test system for obtaining and testing blood samples with minimum user effort is described.

BACKGROUND OF THE INVENTION

Analyte concentration determination in physiological samples is of ever increasing importance to today's society. Such assays find use in a variety of application settings, including clinical laboratory testing, home testing, etc., where the results of such testing play a prominent role in the diagnosis and management of a variety of disease conditions. Analytes of interest include glucose for diabetes management, cholesterol for monitoring cardiovascular conditions, drugs for monitoring levels of therapeutic agents or identifying illegal/illegal levels of drugs, and the like. In response to this growing importance of analyte concentration determination, a variety of analyte concentration determination protocols and devices for both clinical and home testing have been developed.

In determining the concentration of an analyte in a physiological sample, a physiological sample must first be obtained. Obtaining and testing the sample often involves cumbersome and complicated procedures. Unfortunately, successful manipulation and handling of test elements, lancing members, meters and the like is to a great extent dependent on the visual acuity and manual dexterity of the user, which in the case of people with diabetes is subject to deterioration over the course of the disease state. In extreme cases people that have significant loss of sight and sensation, testing procedures can become significantly difficult and requires additional assistance from ancillary devices or personnel.

A typical procedure involved with making a glucose measurement involves the following actions or steps (but not necessarily in the order given):

1) removing supplies from a carrying case,
2) removing a lancing device loading cap or door,
3) removing and disposing of an old lancet form the lancing device,
4) inserting the lancet in the lancing device,
5) twisting off a protective cap from the lancet,
6) replacing the lancing device cap.
7) cocking the lancing device,
8) opening a test strip vial/container,
9) removing a strip from the container and inserting or interfacing it with a meter,
10) holding a lancing device to the skin,
11) firing the lancing device,
12) lifting the lancing device and setting aside,
13) extracting a sample,
14) applying sample to the test strip and getting results,
15) disposing of the test strip,
16) cleaning the test site, and
17) returning supplies to the carrying case.

Sometimes fewer steps are involved. One manner of reducing the number of actions is by integrated devices set to combine multiple functions.

In this regard, certain test strip dispensers are configured to both store and advance successive test strips upon actuation. Examples of such devices are presented in U.S. Pat. Nos. 5,510,266; 5,575,403, 5,797,693 and possibly in PCT Publication WO 01/63272. In addition some dispensers also include meter functionality. Examples of such of systems that integrate test strip meter and dispenser combination functions are disclosed in U.S. Pat. Nos. 5,736,103, 5,757, 666 and PCT Publication WO 99/44508. Furthermore, the device described in WO 01/23885 includes all of the above features, plus a receptacle to receive spent test strip elements that are cut off of a continuous roll of the same.

Another class of devices designed to decrease the number of steps required in test strip use includes automatic or semi-automatic lancing devices. U.S. Pat. No. 6,228,100 discloses a structure configured for sequential firing of a number of lancets, one at a time, in order to eliminate the requirement that a user remove and replace each lancet individually before and after use.

The device disclosed in U.S. Pat. No. 5,971,941 attempts to combine the functionality of each of the preceding classes of test strip devices. In effort to provide an "integrated" system for sampling blood and analysis thereof, it includes a magazine of test strips, test strip advancement and dispensing features, a meter with a display and an automated lancing mechanism all housed with a single box. While presenting some measure of advance in user convenience, the test strip and lancing features are removed from each other causing the user to take two steps in lancing and transferring sample to a test strip. Furthermore, the device includes no provisions for used test strips.

While certain combination test strip and lancing systems that do not require that a subject to move the device relative to the sample site in use (e.g., the systems described in U.S. Pat. Nos. 6,352,514; 6,332,871; 6,183,489; 6,099,484; 6,056,701 and 5,820,570), some of these systems are quite complex and, consequently, either difficult to operate or costly to produce. In addition, some involve changing-out spent test and/or lancet members one-at-a-time. This is true with respect to the systems described in U.S. Pat. Nos. 6,027,459; 6,063,039; 6,071,251 and 6,283,926 as well as for certain embodiments disclosed in PCT Publication WO 01/64105.

However, another embodiment presented in that reference provides for multiple lancet/sensor pairs that only need to be changed out after the disks including each are spent. An exemplary number of a dozen such radially-oriented pairs is provided. PCT Application entitled "Analyte Measurement," claiming a priority of Dec. 19, 2000 from GB 0020929.4 also discloses a meter including a multiple sensor/tester element. Fluid extracted from a subject by a microneedle at a common entrance port is selectively switched between a number of microchannels by means of electro-osmotic pumps and hydrophobic gates. The present invention is distinguished from each of these inventions in terms of its modular use of combination test strip and sensor elements, in which unexposed items may be sealed-off from contamination, and possibly provided in greater number, as well as in the simplicity of the present invention which preferably involves mechanical movement for sample acquisition and handling.

Of course, such advantages may be present in systems according to the invention in various degrees. It is intended that, in one way or another, the invention is of assistance in reducing barriers to patient self-monitoring and therefore result in improved outcomes in the management of disease, such as diabetes.

SUMMARY OF THE INVENTION

A preferred variation of the invention truly minimizes the steps required for analyte test strip use as defined above. As practiced with each of the optional features, the present invention merely involves four such user steps. These include: providing a system according to the present invention, placing it against a test site, pushing the system body portions together and reading a test result. The system is then removed and put away. It may include a cap to be removed initially and replaced finally.

In a preferred variation of the invention, such a cap includes a magazine that automatically receives spent or used test strips. In another variation of the invention (one in which test strips are merely ejected) a user disposal step may be added.

The system of the present invention utilizes disposable test strip elements that include an integral lancet. Examples of such strips include those described in U.S. patent application Ser. Nos. 09/919,981, (now abandoned), 09/923,093, (now abandoned) 10/143,399, (now abandon). The needle may be configured to collect blood, interstitial fluid, other body fluids, or any combination thereof. Regardless of the type of strip chosen and sample to be collected, the members are stored in a magazine, from which they are fired to produce a wound to receive sample therefrom.

The action provided by the meter/dispenser of the present invention is preferably implemented by a series of links, levers and spring elements such that advancement of an upper body portion relative to a lower body portion resting against a test site causes a test strip to be taken from the magazine advanced to form a stick and collect sample. Following such action, the meter may be removed, test results are displayed and such action as desired to dispose of the used test strip occurs.

BRIEF DESCRIPTION OF THE DRAWINGS

Each of the figures diagrammatically illustrates aspects of the invention. To facilitate understanding, the same reference numerals have been used (where practical) to designate similar elements that are common to the figures. Some such numbering has, however, been omitted for the sake of drawing clarity.

FIGS. 1B, 2B, 3B, 4B, 5B, 6B, 7B, 7D, 8B, 9B and 10A are top-down cross sectional views of system(s) according to the present invention at various stages of operation.

DETAILED DESCRIPTION OF THE INVENTION

In describing the invention in greater detail than provided in the Summary above, details of an embodiment of the invention together with aspects of system use. Two alternate variations of the invention are described in this manner, though other variations are possible. Finally, examples of a preferred test strip for use in the device are disclosed.

Before the present invention is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "and," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Last, it is to be appreciated that unless defined otherwise, all technical and scientific terms used herein have the same meaning as commonly understood by one of ordinary skill in the art to which this invention belongs.

Device and System Use

Figure 1A:
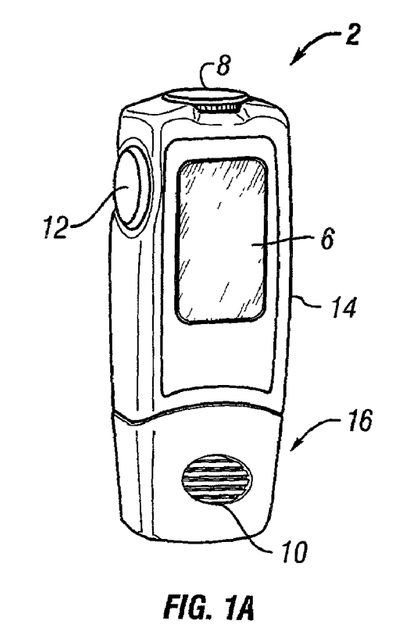
FIGS. 1A, 2A, 3A, 4A, 5A, 6A, 7A, 7C, 8A, 9A and 10A are perspective views of system(s) according to the present invention at various stages of operation.
Figure 1B:
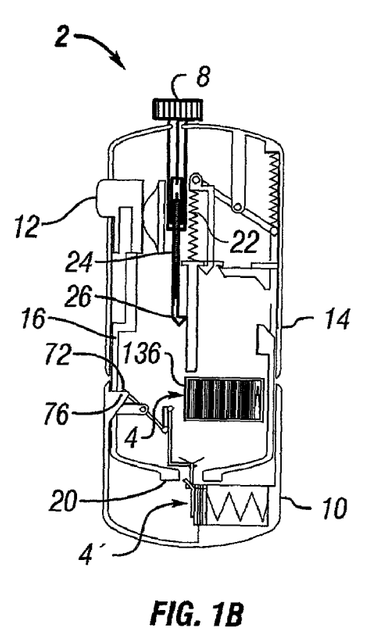

Turning now to FIGS. 1A and 1B an exemplary system 2 according to the present invention is disclosed. The device is a meter that includes actuation features for firing test strips 4. A screen 6 is provided to display meter results and/or direct user action in connect with system 2 use. Other externally visible features include optional adjustment knob 8, cap 10 and interlock button 12.

Figure 2A:
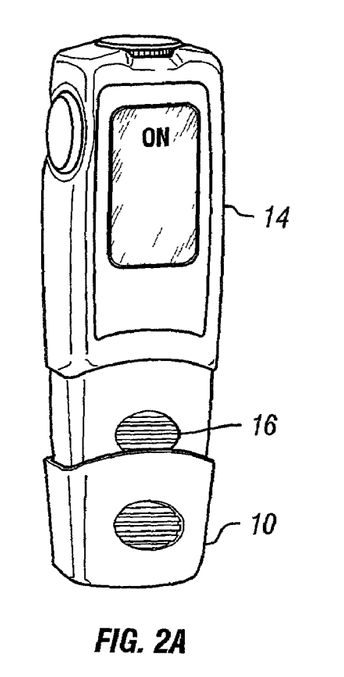

Whether all or none of these optional features are included, system 2 comprises an upper body portion 14 and a lower body portion 16. As shown in FIG. 2A, the lower body portion is exposed upon removal of cap 10.

In operation, lower body portion 16 is slidingly received by upper body portion 14. The relative motion between these two members actuates the various elements within system 2. As described further below, the mechanism enables combination of two steps involved in lancing: namely the cocking of the launcher mechanism and the release of the launcher. Specifically, a single motion first cocks the mechanism and later releases the cocked mechanism. This design approach is similar to that of a center punch used in creating an indentation on a surface. In combination with a test strip integrating a biosensor and lancet, pressing system 2 against the surface of the skin leads to a single step in performing a procedure that normally involves in excess of 10 to 15 steps.

As shown in FIGS. 1A and 1B, system 2 is in an "off" mode. In this mode, knob 8 is preferably actuated by turning clockwise or counterclockwise to set the depth, or any other variable that may be necessary to adapt to a specific user (e.g., force on a pressure-ring), to which a lance portion 18 of test strip 4 will fire relative to a face 20 of the system. Face 20 may serve as such a "pressure ring" in that when it is applied to the skin surface, it depresses tissue around a periphery of the intended wound site. The force on pressure ring may be dictated by the compression force to slide the lower portion into the upper portion; upon application of this force, the test strip is typically also launched into the skin. The pressure formed at the site to be lanced, resulting at least in part from stretching the skin in this area, is useful for extracting a sample in that it helps "pump" material from the wound produced.

Wound/penetration depth is preferably set to between about 0.02 mm and 2.0 mm, or more preferably set between 0.5 mm and 1.5 mm, by virtue of a screw-type interface 22 which advances or retracts an extension 24 carrying a stop portion 26. Such adjustment action usually accomplished at this stage is indicated by the use of bold in connection with the elements at issue.

Figure 2B:
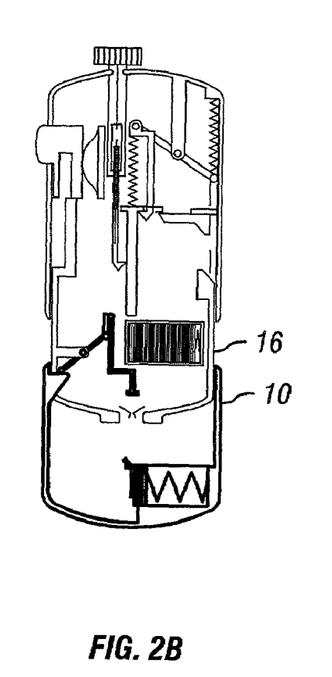

FIGS. 2A and 2B show cap 10 being removed from system 2. It is slidingly received by lower body portion 16. Detent features may be provided in order to prevent inadvertent separation of the elements.

Removal of cap 10 preferably turns the system "on" as indicated in FIG. 2A. Where no cap is provided, another preliminary action may be required to activate the system (such as depressing a button) or system 2 could be activated by subsequent activity that is described.

In any event, as shown in the other figures, various user directions or messages may be displayed by the meter. In addition to displaying test results and directions, display 6 may present information regarding the number of test strips left, time to expiration, etc.

Figure 3A:
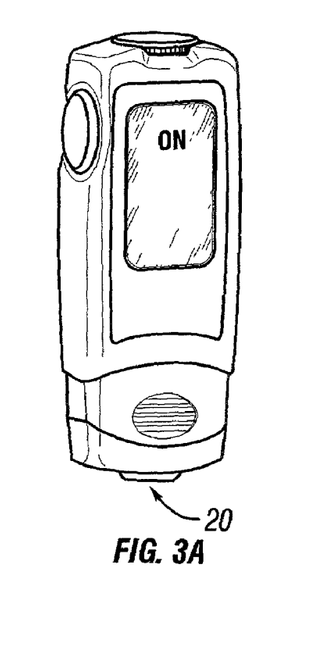
Figure 3B:
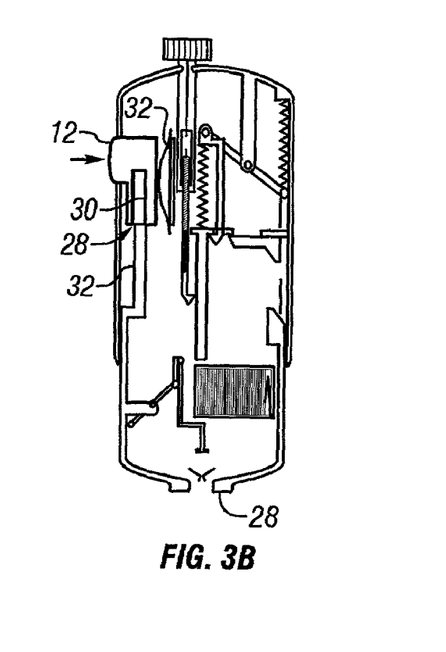

FIG. 3B illustrates actuation of button 12 for a different purpose (though, it could be used to turn the system on as well). When a user depresses button 12 as shown, an interlocking interface 28 formed by an extension 30 of button 12 and another extension 32 of lower body portion 16 is released. A spring member 34 may be provided to bias the button outwardly.

Any form of spring may be used in this regard. The same is true for other springs employed in the invention. By varying the internal configuration of system 2 flat springs, leaf springs, coil springs, torsion springs or extension springs may be used. What is more, metal or polymer spring members may be interchangeably used.

Regardless of such constructional details, with face 20 exposed and interlock or safety mechanism 28 set free (most preferably by depressing button 12) the face is set against a target site. Such a target site might be a patient's or user's finger, forearm, palm, or elsewhere.

Figure 4A:
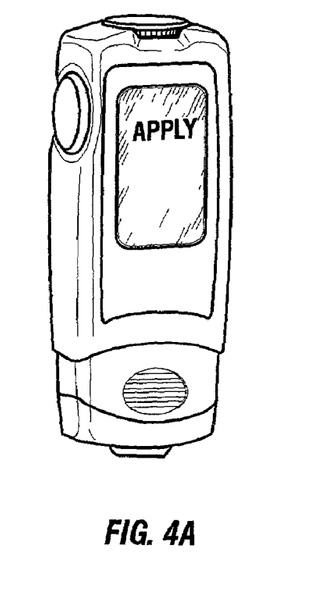
Figure 4B:
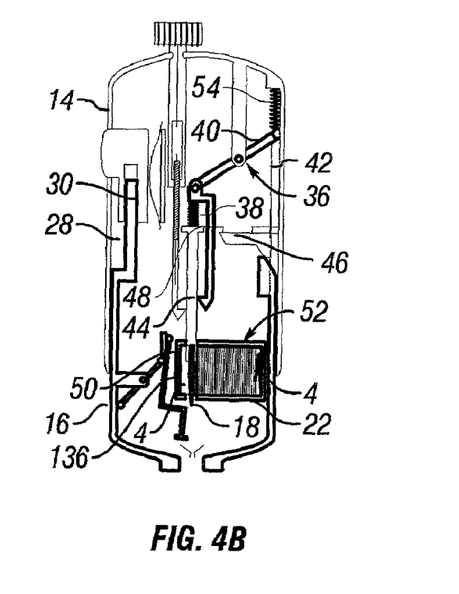

With system 2 so positioned an "apply" message may appear on screen 6 as shown in FIG. 4A. Whether prompted in this manner or not, FIG. 4B shows the next action taken by a user. Here, upper body portion 14 is pushed toward the target site. This causes system 2 to collapse, with lower body portion 16 slidingly received within upper body portion 14.

Such user activity results in several actions within device 2. For one, interlock portions 28 and 32 slide past each other (instead of interfering with each other's movement). In addition, a lancing mechanism 36 within system 2 is cocked. This is accomplished by stressing launch spring 38. While this may be accomplished otherwise, in the variation of the invention shown here, a lever arm 40 driven by a cocking extension 42 of lower body portion 16 provides the input. A lance interface member 44 is held in a cocked position by a latch 46 and cooperative catch 48 at one end of the interface member.

At the other end of interface member 44, test strip interface features 50 are provided. These pick up or interface with a test strip 4. As shown, interface features advance a test strip slightly relative to other test strips contained within a magazine 52.

The magazine may be configured in any convenient manner to allow loading of a large number of test strips therein (e.g., between about 10 and 100, more preferably between 15 and 25) and release therefrom. Providing numerous test strips as possible in view of the magazine format employed by the present invention allows for greatly increased user convenience.

Magazine 52 is preferably spring-loaded in order to function properly regardless of orientation. The magazine preferably has a door 136, which remains closed except during brief periods of time when the test strip is removed, serves as a moisture barrier. (A similar door or barrier may be provided for waste magazine 22). Also, a drying agent (e.g., a desiccate) may be contained within the magazine to protect the test strips' reagent from moisture. To further preserve the integrity of unused test strips, the mechanism driving the test strip and operating the door is preferably configured so it will not leave a test strip partially advanced or the magazine open if the user were not to complete the total relative motion of sliding lower portion 16 into upper portion 14.

Figure 10A:
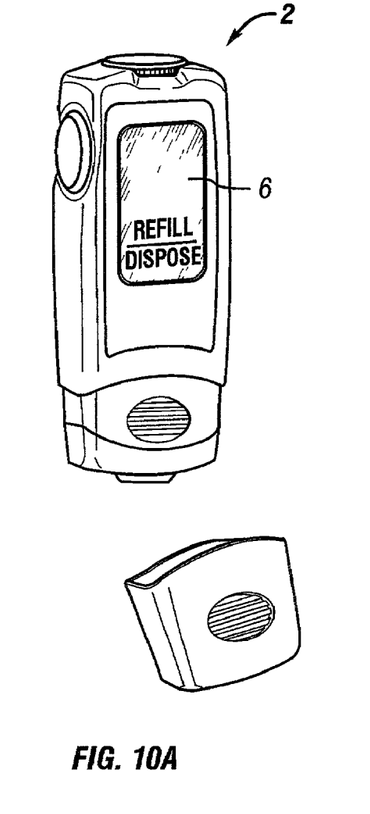

The magazine, may take the form of a removable cartridge or cassette as shown in FIG. 10A described further below. Especially under such circumstances, it may contain a barcode or some other means (such as a chip) for transferring information to the meter upon loading the same with test strips or a strip cartridge. In which case, the meter would automatically read this information when the magazine/cartridge is loaded into the system, via an optional detection system 138 (shown in FIG. 10B). Any conventional reader or placement as appropriate to the media by which the information is expressed may be employed. Regardless of such constructional details, examples of information that may be useful include: a calibration factor or code, number of strips remaining/used in magazine, number of days since magazine was installed and/or days until strip expiration (such as a hard date or a date that is a function of when the magazine was loaded into the system).

Further optional feature(s) that may be included in meter 2 include diagnosis or calibration system(s). For example, system 2 may include features to determine if it is working properly in reference to one or more control species, such as a control solution comprising glucose of a known concentration.

The relative motion between body portions 14 and 16 also results in cocking or loading a return spring 54. Its use will be described further below.

Figure 5A:
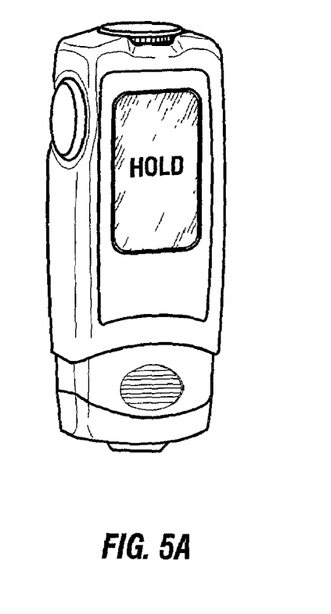
Figure 5B:
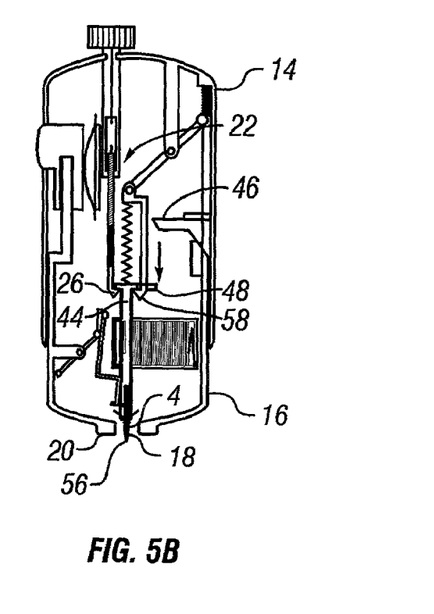

FIGS. 5A and 5B, show activity in connection with lance/test strip firing preceding such action. In one variation, motion of the lower body portion 16 cams latch 46 to release spring loaded interface member 44 to travel, push magazine door 136 open, and pick-up a strip to advance it out of the magazine. Alternately, an electronic solenoid (not shown) activated by electronics included in system 2 can be utilized to release latch 46, whereupon interface member 44, together with test strip 4 advances as indicated. As it advances toward the skin, interface member 44 preferably urges the test element through guides 78.

In use, since only the needle end of a test element/strip comes in contact with a user, the opposite end of the device adjacent interface member 44 does not into contact with body fluids. Accordingly, this element is not able to contaminate unused test strips upon retraction past the same. Further, magazine door 136 is opened only for a very short time period, thereby minimizing opportunity for contamination. In addition (as further described below), used test strips are ejected from the system or stored in a (sealed) magazine in the cap and are never brought near the magazine. All of these factors may contribute to maintaining unused test strip quality.

A tip 56 of the lance portion of the test strip is shown protruding slightly from the face 20 of system 2. As shown in FIG. 5A, the meter screen preferably directs a user to hold the device in place. This allows time for sample collection from the wound produced, such as by a pressure-ring to force fluid from the wound and capillary action along the lance member 18. Still, it is to be noted that other driving forces, such as vacuum, may be employed to facilitate sample acquisition.

Figure 6A:
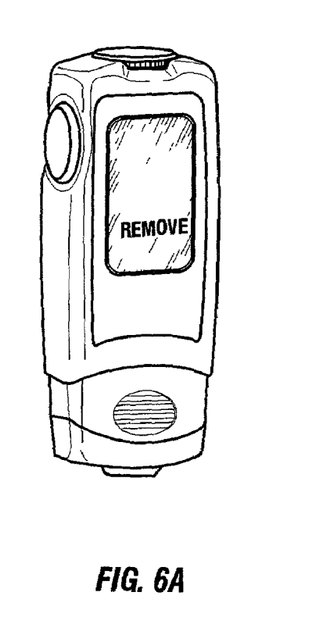
Figure 6B:
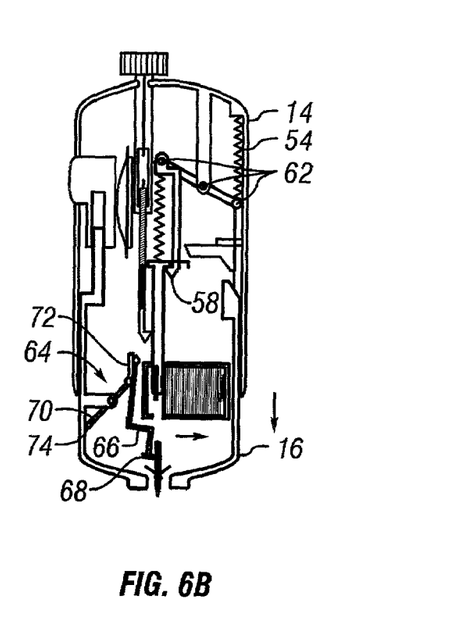

Following a sufficient time interval, (e.g., usually between about 0.1 and 15 seconds, preferably less than 3 seconds), as shown in FIG. 6A, the system preferably directs the user to remove system 2 from the test site. By such action, as shown in FIG. 6B, lower body portion returns to its pre-compressed state. Preferably return spring 54 urges the body portions away from each other as shown. As the body portions separate, an interface member return catch 58 withdraws interface member 44. Catch 58 is preferably provided at an end of a return member 60 that is actuated by lever 40, which is, in turn, associated with lower body portion 16. Pivoting interface portions 62 are preferred, though the parts may be integrally molded with living hinge sections or otherwise produced.

In addition to showing the movement of the body portions relative to each other in an intermediate state, FIG. 6B shows a test strip disposal mechanism 64 as it swings into position for action. The mechanism may comprise a pusher arm 66 with a stop or interface portion 68, a lever arm 70 and an intermediate link 72. These members may also be spring-loaded. Furthermore, there construction may vary in like manner to the other components noted directly above.

Figure 7A:
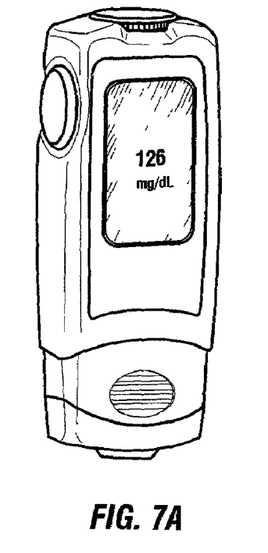
Figure 7B:
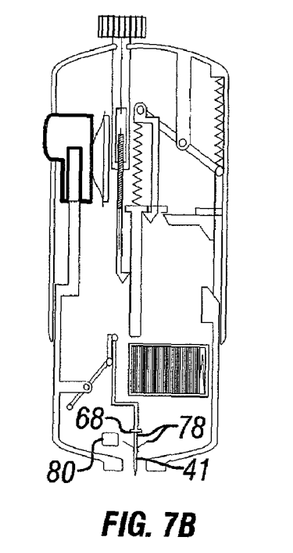

In order for the members of the disposal mechanism to reach the location shown in FIG. 6B, as it progresses to that shown in FIG. 7B (or 7D), certain antecedent actions may have occurred. These are illustrated in connection with FIGS. 1B, 2B and 4B.

In FIG. 1A, disposal mechanism 64 is shown at a rest position. A protrusion 74 at the end of lever arm 70 is interfaced with a complementary pusher portion 76 of cap 10 (see FIG. 1B). Upon removal of the cap, the disposal mechanism moves to the position shown in FIG. 2B. From here, it is able to swing out of the way of lance firing as shown in FIG. 4B. Ultimately, as illustrated in FIG. 6B, it moves into position as seen in FIG. 7B.

In FIG. 7B, interface portion 68 is shown interfacing with a used strip 4'. The strip is at least partially confined by optional opposing guide members 78. In this location an adjacent meter element 80 may be used to read the strip especially where colorametric sensors are employed. Alternately, where electrochemical test strips are used, the guides 78 may serve the dual purpose of directing the test strip and also serving as electrical contacts to interface electrochemical strips to the meter, when this type of strip is used.

The result obtained (or a result derived from the data obtained) is displayed on screen 6 as shown in FIG. 7A.

Figure 7C:
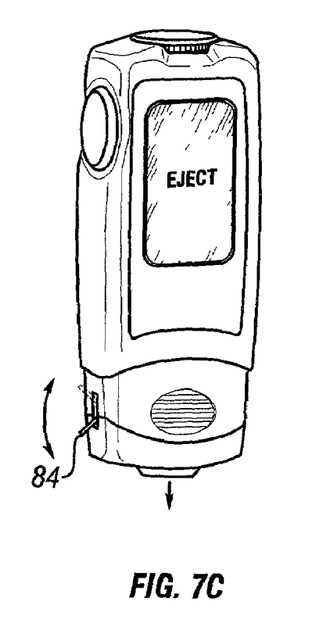
Figure 7D:
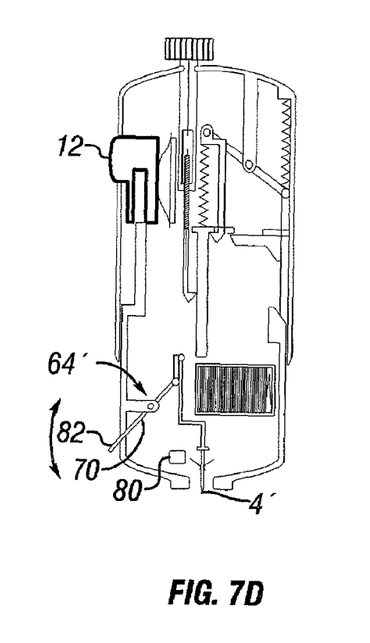
Figure 8A:
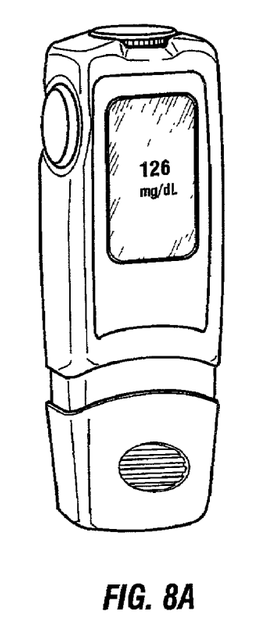
Figure 8B:
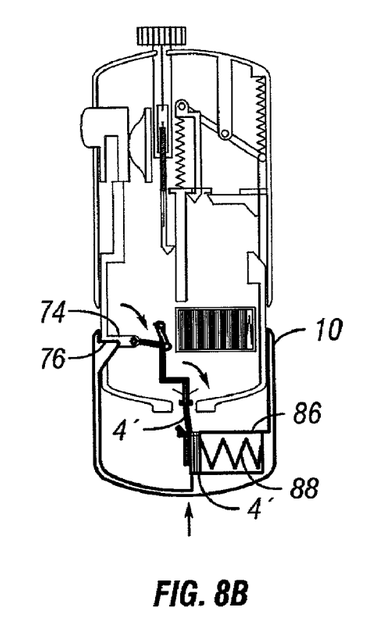

In the variation of the invention in FIGS. 7C and 7D, meter functionality may be identical to that in FIGS. 7A and 7B. However, in the variation shown in FIGS. 7C and 7D, the disposal mechanism 64' is configured somewhat differently. The primary distinction is observed in connection with extension 82 off of lever arm 70. Instead of being configured to interface with a cap, lever the extension make lever 70' suitable for manual operation. It is preferably actuated as indicated by the double-headed arrow along slot 84 shown in FIG. 7C to eject spent test strips from system 2. Before actuating the lever extension, it is preferred that a user direct the device toward a suitably waste receptacle.

Figure 9A:
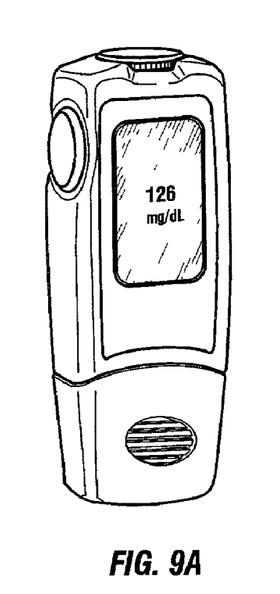
Figure 9B:
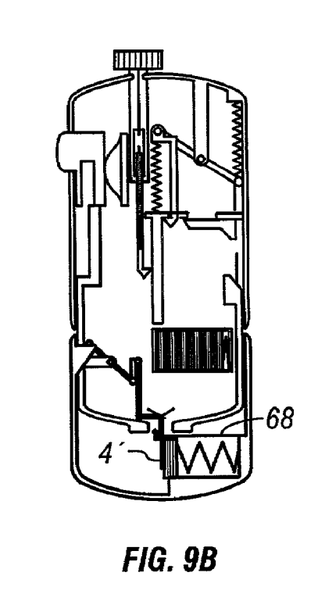

Whether or not manual test strip disposal features are included in system 2, it may be preferred to include waste magazine 86 in cap 10. Such a magazine is used as shown in FIGS. 8A-9B. At any time after system 2 is removed from the test site (for instance, in response to meter screen directions provided in FIG. 6A), cap 10 may be replaced. In doing so tab or protrusion 74 of lever arm 70 is captured by cap interface 76. This advances pusher arm 66, causing interface section 68 to drive spent test strip 4' into waste magazine 86. The addition of spent strips to its cache of spent strips held in place by biasing spring 88 eventually fills the magazine. FIGS. 9A and 9B show cap 10 in place with system 2 restored to its configuration in FIGS. 1A and 1B. At this point, spent strip 4' is fully deposited within magazine 86. When the magazine is full, cap 10 may be thrown away en Toto. Such activity is shown in connection with FIGS. 10A and 10B.

Alternately, the magazine itself may be disengaged from the cap and be thrown away alone. Either way, used test strips thus-packaged for disposal minimize any disposal issues that are presented.

Still, at least in connection with the system approach taught in FIGS. 7C and 7D, it may be preferred no cap 10 is provided, thereby somewhat simplifying operation of the system. Still, it is possible to provide a system that includes a waste magazine and the ability for the user to individually dispose of test strips, as desired. Regardless, where manual test strip disposal features are provided as shown in FIGS. 7C and 7D, release of button 12 to reactivate interlock 28 prior to actuating lever arm extension 82 is advised in order to prevent inadvertent movement of the body portions with respect to each other.

Figure 10B:
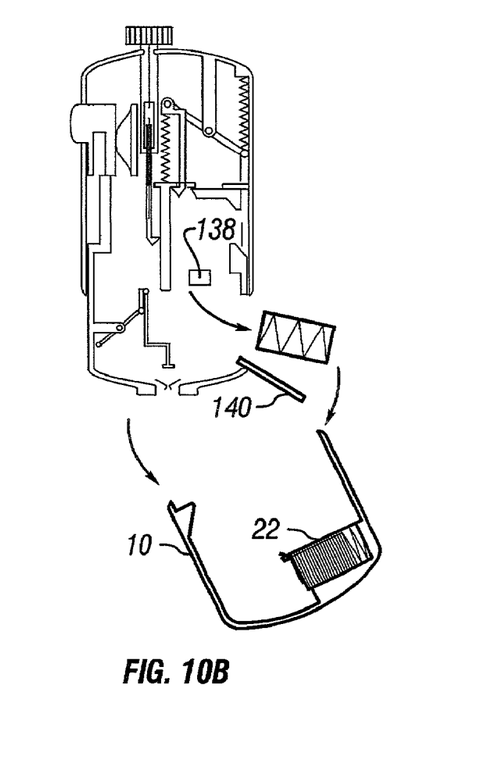

Furthermore, one or both of the magazines may be manually inserted and/or removed in/from their respective housing portions. In either case, a detent mechanism or finger-actuated latch (not shown) may be provided to ensure retention. Removal of an empty cartridge 52 from the upper body portion is shown in FIG. 10B. Upon opening a door 140, an empty unit may be discarded in favor of a full one or simply reloaded and replaced in the system. Utilizing a new cartridge marked with identification data as discussed above is, however, preferred.

As shown in FIG. 10, action associated with refill, replacement or disposal of test strips or ancillary equipment may be indicated on readout 6 when appropriate. Alternately, or additionally, magazines 22 and/or 52 may be produced with transparent material or an indicator may be provided to inform a user of its status. A open or transparent window in cover 10 or the body of the meter may be employed to allow the user to observe the quantity of unused strips in the magazine(s)/cassette(s).

Test Strips

As noted above, many types of test strips which integrally include a biosensor and a forwardpointing lance member may be used in the present invention. However, of the examples given, those described in U.S. Pat. No. 10/143,399 entitled Physiological Sample Collection Devices and Methods of Using the Same, may be most preferred. Details regarding the production and use of such devices are presented therein. Regardless a brief description is provided below.

Figure 11A:
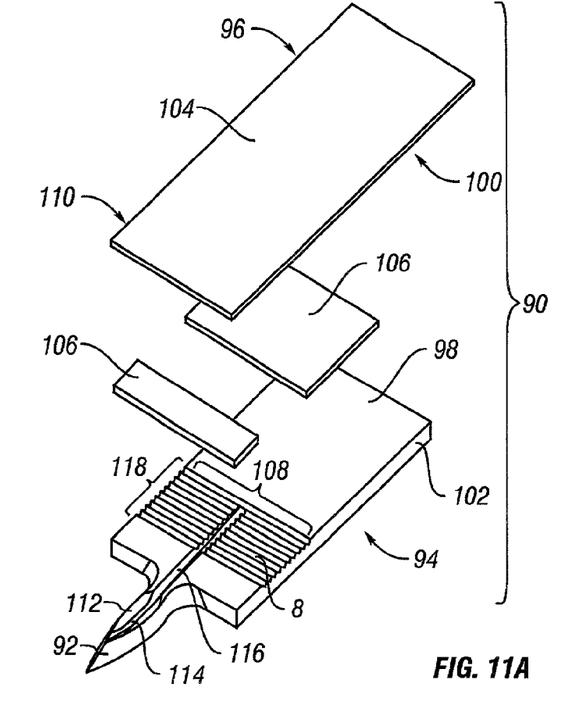
FIGS. 11A and 11B are perspective views of a preferred test strip for use in the present invention.
Figure 11B:
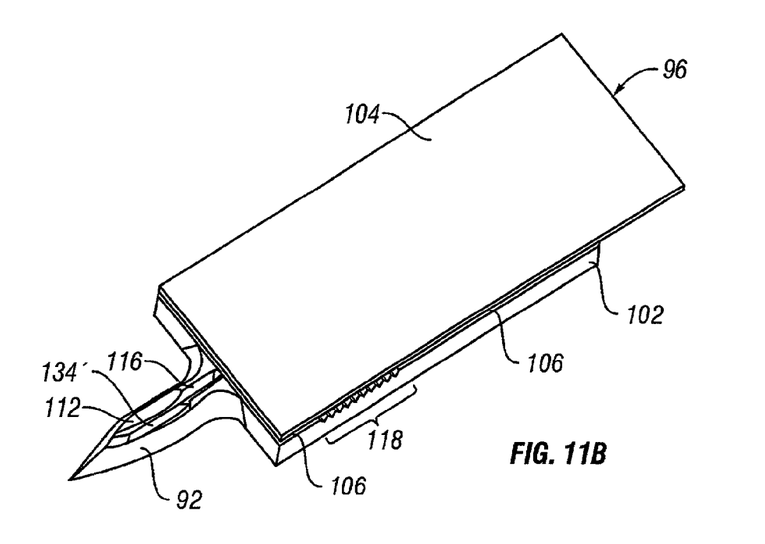

FIGS. 11A and 11B illustrate such an exemplary test strip or biosensor device 90 fully described in the above-referenced case. Device 90 includes an electrochemical test strip configuration and a microneedle 92 integrated therewith. The biosensor is defined by an electrochemical cell generally having two spaced-apart and opposing electrodes 94 and 96, respectively referred to herein as bottom electrode 94 and top electrode 96, though in use they may oriented in any direction. At least the surfaces of electrodes 94 and 96 facing each other are comprised of a conductive layer 98 and 100, respectively, such as a metal, deposited on an inert substrate 102 and 104, respectively. The spacing between the two electrodes is a result of the presence of a spacer layer 106 positioned or sandwiched between electrodes 94 and 96. Spacer layer 106 preferably has double-sided adhesive to hold the electrodes. The spacer layer is preferably configured or cut so as to provide a reaction zone or area 108. A redox reagent system or composition 110 is present within reaction zone 108, where the reagent system is selected to interact with targeted components in the fluid sample, typically whole blood, during an assay of the sample. Redox reagent system 110 is usually deposited on the conductive layer 100 of top electrode 96 wherein, when in a completely assembled form (as shown in FIG. 10B), redox reagent system 110 resides within reaction zone 108. With such a configuration, bottom electrode 94 serves as a counter/reference electrode and top electrode 96 serves as the working electrode of the electrochemical cell. However, in other embodiments, depending on the voltage sequence applied to the cell, the role of the electrodes can be reversed such that the bottom electrode serves as a working electrode and top electrode serves as a counter/reference electrode.

Microneedle 92 is preferably integrally formed with and extends from bottom electrode 94. The microneedle is shown with a space-defining configuration in the form of a concave recess 112 within its top surface. The recess creates a corresponding space within skin tissue upon penetration of microneedle 92 into the skin. This space acts as a sample fluid collection reservoir wherein fluid released upon penetration is pooled within the space prior to transfer into the electrochemical cell. An opening 114 to further expose the pooling area defined by recess 112 to the outside environment may also be included, thereby increasing the volume and flow rate of body fluid into the pooling area.

Biosensor device 90 further includes a sample fluid transfer or extraction pathway or channel 116 which extends from recess 112 to within the biosensor. At least a portion of a proximal end of the pathway resides within the biosensor portion of device 90, specifically within reaction zone 108, and a portion of a distal end of pathway 114 resides within microneedle 92. Pathway 116 is dimensioned so as to exert a capillary force on fluid within the pooling area defined by recess 112, and draws or wicks physiological sample to within the reaction zone. Extending laterally from proximal portion 114 of the pathway to within a portion or the entirety of the reaction zone are sub-channels 118. The sub-channels facilitate the filling of reaction zone 108 with the sampled fluid.

Figure 12A:
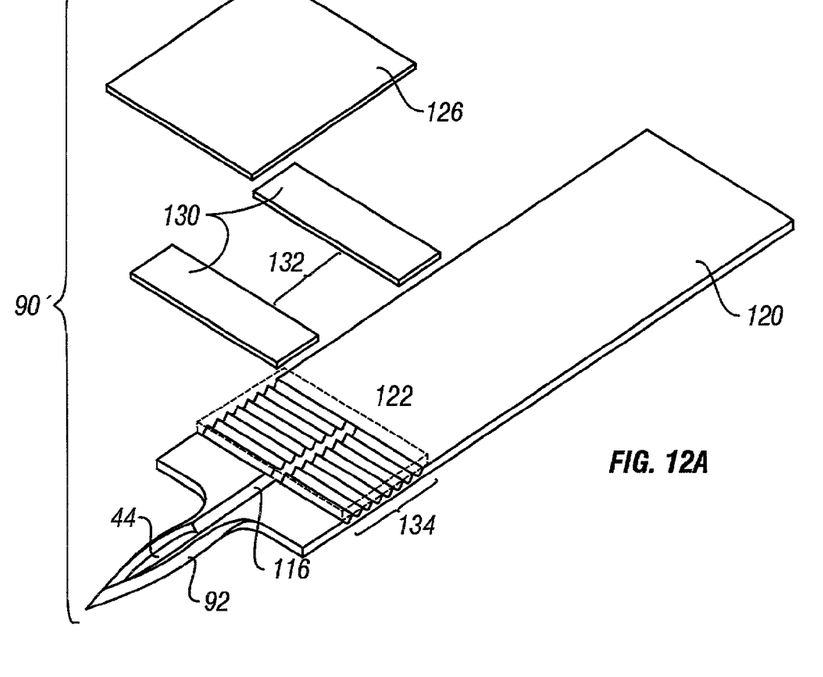
FIGS. 12A and 12B are perspective views of another preferred test strip for use in the present invention.
Figure 12B:
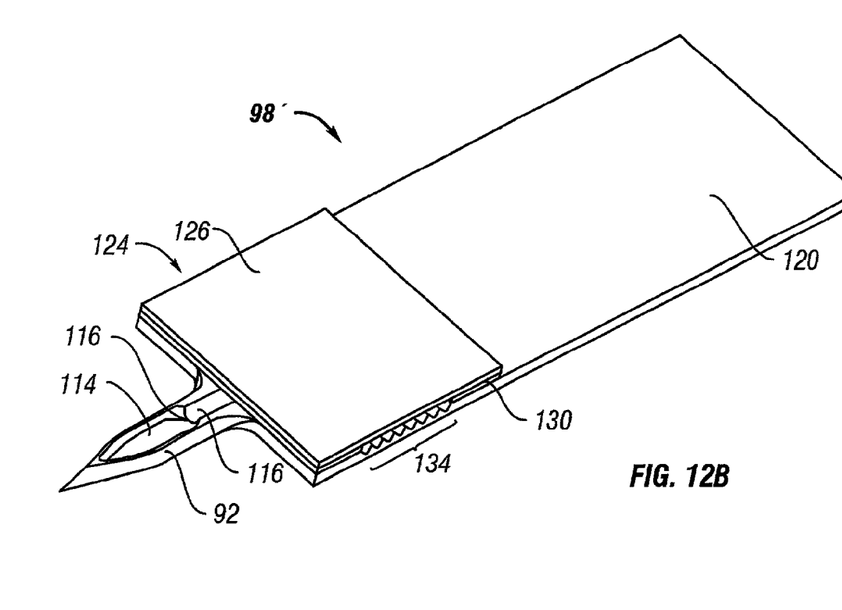

FIGS. 12A and 12B illustrate another suitable embodiment of a biosensor/skin-piercing device 90' which is also disclosed in U.S. patent application Ser. No. 10/143,399, entitled Physiological Sample Collection Devices and Methods of Using the Same. Device 90' has a photometric/colorimetric biosensor configuration and a microneedle 92' integrated therewith. The calorimetric or photometric biosensor is generally made up of at least the following components: a support element or substrate 120 made of either an inert material, including suitable plastics, or a metal material, a matrix or matrix area 122 for receiving a sample, a reagent composition 124 within the matrix area, the reagent composition typically including one or more members of an analyte oxidation signal producing system, an air venting port (not shown) and a top layer 126 which covers at least matrix 122. In some embodiments, top layer 126 may be a membrane containing a reagent composition impregnated therein while the matrix 122 may or may not contain reagent composition. Further, test strip 90' may include a double-sided adhesive layer 128 situated between substrate 120 and membrane 126 to hold them together. Double-sided adhesive layer 130 has a cut-out portion 132 which corresponds to the area of matrix 122 and defines an area for deposition of the sampled physiological fluid and for the various members of the signal producing system.

Microneedle 92 is preferably formed with and extends from substrate 120 and has a space-defining configuration in the form of an opening 114 which extends transverse to a dimension, e.g., width or thickness, of microneedle 92'. As with recess 112 of microneedle 90 above, opening 114 forms an open space within the tissue upon penetration of the microneedle into the skin. Such open space acts as a sample fluid collection reservoir wherein fluid released upon penetration is pooled within the space prior to transfer into the photometric/calorimetric cell. Note, however, that the needle variation shown in FIGS. 11A and 11B may instead rely solely on a recess and omit a through-hole.

Biosensor device 90' hosts a sample fluid transfer or extraction pathway 116 having a distal end which extends within a portion of microneedle 92' and terminates at a distal opening 114. At least a portion of the proximal end of pathway 116 resides within the biosensor portion of device, specifically within matrix area 122. Pathway 116 is dimensioned so as to exert a capillary force on fluid within the pooling area defined by opening 114, and draws or wicks physiological sample to within matrix area 122. Extending laterally from proximal portion of pathway 116 to within a portion or the entirety of matrix area 122 are sub-channels 134, which facilitate the filling of matrix or matrix area 122 with the sampled fluid.

CLAIMS

Though the invention has been described in reference to certain examples, optionally incorporating various features, the invention is not to be limited to the set-ups described. The invention is not limited to the uses noted or by way of the exemplary description provided herein. It is to be understood that the breadth of the present invention is to be limited only by the literal or equitable scope of the following claims.

That being said, we claim:

1. An analyte detection system comprising:
   a first body portion comprising a lancing mechanism that comprises a lever arm pivotably connected to said first body portion and operatively connected at a first end of said lever arm to a test strip interface member by a launch spring;
   a second body portion slidably received by said first body portion, the second body portion comprising a cocking extension; and
   a magazine adapted to receive a plurality of unused test strips;
   wherein the cocking extension of said second body portion is engageable with a second end of said lever arm of said lancing mechanism to pivot said lever arm to advance said interface member to take a test strip from said magazine and advance said test strip along a lancing path.

2. The system of claim 1, wherein said magazine is carried by said second body portion and wherein said second end of said lever arm is actuatable by said second body portion to pivot said lever arm and load said launch spring between said first end of said lever arm and an end of said interface member for firing a test strip to position at least a lance portion of the test strip past a face of said second body portion to penetrate a tissue site.

3. The system of claim 1, further comprising a button, wherein said body portions are adapted to be moveable relative to each other upon depressing said button.

4. The system of claim 1, further comprising a meter test element and a meter screen.

5. The system of claim 1, further comprising a test strip disposal mechanism including a pusher arm with a disposal interface portion, a disposal lever arm, and an intermediate link between said disposal lever arm and said disposal interface portion.

6. The system of claim 5, wherein said disposal mechanism is adapted to be actuated manually by an extension from said disposal lever arm.

7. The system of claim 5, wherein said disposal mechanism is adapted to be actuated by an interface portion of a cap.

8. The system of claim 1, further comprising a cap.

9. The system of claim 8, wherein said cap carries a second magazine adapted to receive a plurality of used test strip members.

10. The system of claim 9, further comprising a test strip disposal mechanism adapted to deposit used test strips in said second magazine.

11. The system of claim 10, wherein a test strip disposal mechanism includes a pusher arm with a disposal interface portion, a disposal lever arm, and an intermediate link between said disposal lever arm and said disposal interface portion.

12. The system of claim 11, wherein said disposal mechanism is adapted to be actuated by an interface portion of said cap.

13. The system of claim 1, wherein said magazine comprises a door openable by said test strip interface member.

14. A method of collecting a biological sample from a test site, said method comprising:
   providing a system according to claim 1;
   placing said second body portion face against a tissue site; and
   forcing said body portions toward each other to cock and fire a test strip into the tissue site, wherein a lance portion penetrates said tissue site and a biological sample is taken from said tissue site and transported to a biosensor portion of said test strip.

15. The method of claim 14, further comprising:
   storing said test strip in a second magazine after use.

16. The method of claim 15, wherein said system further comprises a cap containing said second magazine, the method further comprising replacing said cap after storing a test strip.

17. The method of claim 14, wherein said system further comprises a cap, said method further comprising:
   removing said cap to turn on said system.

18. The method of claim 17, further comprising:
   replacing said cap to turn off said system.

19. The method of claim 14, further comprising:
   ejecting said test strip from said system after use.

20. The method of claim 19, wherein said test strip is ejected by manually actuating a lever arm extension.

21. The method of claim 14, wherein a plurality of unused test strips are provided preloaded within said magazine, said magazine being marked with information regarding said test strips, said method further comprising reading said information with said system.

22. An analyte detection system comprising:
   a housing comprising a first housing portion and a second housing portion, wherein said housing portions are slidably engageable with each other, the first housing portion comprising a lancing mechanism having a lever arm pivotably connected to the first housing portion, the second housing portion comprising a cocking mechanism operatively associated with the second housing portion;
   a magazine containing a plurality of unused test strips, said magazine being removably positionable within said housing; and
   a test strip interface member positioned within said housing and operatively connected to the lancing mechanism;
   wherein the cocking mechanism of said second housing portion is engageable with the lancing mechanism of said first housing portion to advance said interface member to take a test strip from said magazine and pass at least a lance portion of a test strip past a face of said second housing portion to penetrate a tissue site.

23. The system of claim 22, wherein said magazine comprises a door wherein advancement of said interface member opens said door.

24. The system of claim 22, wherein said first portion defines a first wall and said second portion defines a second wall, wherein said second wall is received within said first wall.

25. The system of claim 22, further comprising a meter element within said housing for detecting an analyte of a biological sample collected with a test strip.

26. A method of measuring the concentration of an analyte in a sample of biological fluid, said method comprising:
   providing a system according to claim 22;
   placing said second portion face against a tissue site; and
   moving said portions toward each other, wherein said test strip interface member removes a test strip from said magazine and advances a lance portion of said test strip past the second portion face and penetrates said lance portion into said tissue site whereby biological fluid is accessed;
   taking a sample of said accessed biological fluid with said test strip; and
   testing the concentration of sample of said biological fluid.

27. A method of measuring the concentration of an analyte in a biological sample, said method comprising:
  providing a system according to claim 25;
  placing said second body portion face against a test site;
  forcing said body portions toward each other to cock and fire a test strip, wherein a lance portion penetrates said tissue site and a biological sample is taken from said test site and transported to a biosensor portion of said test strip; and
  detecting an analyte in the biological sample.

* * * * *